United States Patent [19]

Albrecht et al.

[11] Patent Number: 4,879,415

[45] Date of Patent: Nov. 7, 1989

[54] PROCESS FOR THE PREPARATION OF CHLORONITROANILINES AND CHLORONITROPHENOLS

[75] Inventors: Bernhard Albrecht, Buus, Switzerland; Jürgen Beyrich, Huttingen, Fed. Rep. of Germany

[73] Assignee: Ciba-Geigy Corporation, Ardsley, N.Y.

[21] Appl. No.: 129,425

[22] Filed: Nov. 25, 1987

Related U.S. Application Data

[63] Continuation of Ser. No. 829,333, Feb. 14, 1986, abandoned.

[30] Foreign Application Priority Data

Feb. 22, 1985 [CH] Switzerland ............................ 827/85

[51] Int. Cl.$^4$ ..................... C07C 85/24; C07C 79/32
[52] U.S. Cl. ..................................... 564/412; 568/709
[58] Field of Search .......................... 564/412; 568/709

[56] References Cited

U.S. PATENT DOCUMENTS

| | | | |
|---|---|---|---|
| 3,929,907 | 12/1975 | Janzon et al. ....................... | 568/709 |
| 4,414,415 | 11/1983 | Aubou et al. ....................... | 564/441 |
| 4,613,698 | 9/1986 | Arndt et al. ....................... | 564/412 |

FOREIGN PATENT DOCUMENTS

| | | | |
|---|---|---|---|
| 0041908 | 12/1981 | European Pat. Off. | |
| 0124084 | 11/1984 | European Pat. Off. | |
| 0161650 | 11/1985 | European Pat. Off. | |
| 432801 | 8/1926 | Fed. Rep. of Germany | |
| 0073742 | 6/1979 | Japan ................................... | 568/709 |
| 1587965 | 4/1981 | United Kingdom | |

OTHER PUBLICATIONS

Chemical Abstract, vol. 51, (Apr. 10, 1957), No. 7, pp. 4765-4766.
Chemical Abstract, vol. 51, (Apr. 10, 1957), No. 7, p. 5008e.
Chemical Abstract, vol. 90, (Apr. 9, 1979), No. 15, Cover page and p. 605, Abstract No. 121176d, "2,6-Dichloro-4-nitroaniline".
Chemical Abstract, vol. 101, (Aug. 27, 1984), No. 9, Cover page and p. 614, Abstract No. 72408r, "Discontinuous Production of 6-chloro-2,4-, etc".
Chemical Abstract, vol. 103, (Oct. 14, 1985), No. 15, Cover page and p. 694, Abstract No. 123139e, "2,6-Dichloro-4-nitrophenol".
Rec. Trav. Chim., 43, 610 (1924).
DE-C-610613 (1.44776.) Kl. 12q, 1o2. I. G. Farbenindustrie Akt. Ges. in Franakfurt A. M., Erfinder: Dr. Gustav Reddelien-Dr. Heinrich Ohlendorf.
Chem Abstracts vol. 81, (1974) Czech 152,603 (CA 84;63329g.
Ullmanns Encyclopadie der technischen Chemie 13, 5ff (1962 Fifth Edition).

*Primary Examiner*—Glennon H. Hollrah
*Attorney, Agent, or Firm*—Kevin T. Mansfield; Edward McC. Roberts

[57] ABSTRACT

The invention relates to a process for the preparation of chloronitroanilines or chloronitrophenols, which comprises chlorinating nitroanilines or nitrophenols in hydrochloric acid by adding simultaneously separate streams of nitroanilines or nitrophenols and of a chlorinating agent to said hydrochloric acid. The process affords pure products in good yield. An accumulation of chlorine during the reaction is avoided.

Chloronitroanilines and chloronitrophenols are useful intermediates for the snythesis of disperse dyes.

9 Claims, No Drawings

PROCESS FOR THE PREPARATION OF CHLORONITROANILINES AND CHLORONITROPHENOLS

This application is a continuation of application Ser. No. 829,333, filed 2/14/86 now abandoned.

The present invention relates to a process for the preparation of chloronitroanilines and chloronitrophenols by chlorinating corresponding nitroanilines or nitrophenols in aqueous hydrochloric acid as reaction medium.

Chlorinated nitroanilines and nitrophenols are important intermediates for dyestuff synthesis and are used in particular for synthesising disperse dyes. Many processes for the preparation of these compounds are described in the literature. A distinction must be made between the direct chlorination of suitable starting compounds and the aminolysis or hydrolysis of appropriate nitrochloro derivatives.

Chlorination yields for example 2-chloro-4,6-dinitroaniline by reacting 2,4-dinitroaniline with potassium chlorate in hydrochloric acid (P. G. van de Vliet, Rec. Trav. Chim. 43 610 [1924]) or with elemental chlorine in water, in the presence of iron(III) chloride (DE-C-610613), and also with dry chlorine in glacial acetic acid in the presence of antimony (CS-A-152 603). Among these chlorination processes the variant using chlorate in hydrochloric acid is widely used. In this process, the 2,4-dinitroaniline is added to hydrochloric acid and the chlorate is slowly added in the form of an aqueous solution. The drawback of this process is, however, that conversion of the starting material to the desired final product is only incomplete. Attempting to improve the conversion by a longer reaction time results in the reaction mass becoming viscous with intermittent foaming, accompanied by evolution of chlorine gas. This method is therefore unsatisfactory with regard to yield and safety.

The chlorination of 2,4-dinitrophenol with elemental chlorine in concentrated hydrochloric acid has also so far not yielded satisfactory results. The formation of chlorinated by-products resulting from the replacement of nitro groups by chlorine groups is observed (published European patent application EP-A 124 084).

Hence it is the object of the present invention to provide a process by means of which nitroanilines and nitrophenols can be reacted substantially completely and which, in addition, is simple and safe to perform.

It has now been found that almost complete conversion of the starting material can be achieved in simple manner and with maximum safety by simultaneously adding separate streams of nitroaniline or nitrophenol and of chlorinating agent to the hydrochloric acid employed as reaction medium. This procedure ensures that the starting material is chlorinated very rapidly, i.e. shortly after addition to the hydrochloric acid in the reactor, so that no accumulation of chlorinating agent in the reaction mixture occurs. Sudden foaming of the reaction mass and the formation of perchlorinated products is thereby largely avoided.

Accordingly, the present invention relates to a process for the preparation of chloronitroanilines or chloronitrophenols by chlorinating the appropriate nitroanilines or nitrophenols in hydrochloric acid, which process comprises charging said hydrochloric acid to the reactor and simultaneously adding separate streams of nitroaniline or nitrophenol and of chlorinating agent.

Suitable starting materials for the process of this invention are preferably mono- or dinitroanilines or mono- or dinitrophenols. Representative examples of such starting materials are: o-, m- or p-nitroaniline, 2,4-dinitroaniline, 2,6-dinitroaniline, 3,4-dinitroaniline, 3,5-dinitroaniline; o-, m- or p-nitrophenol, 2,4-dinitrophenol, 2,6-dinitrophenol, 3,4-dinitrophenol and 3,5-dinitrophenol. In addition to carrying the nitro group, the nitroaniline of the present invention may carry further substituents which are inert under the conditions of chlorination. Particularly good results are obtained in the process of this invention with 2,4-dinitroaniline as well as with p-nitrophenol. These compounds can be reacted to give very good yields of the compounds which are chlorinated in the 6- or 2,6-position.

The starting compounds are known or they can be obtained by known methods. For example, 2,4-dinitroaniline is obtained by heating 4-chloro-1,3-dinitrobenzene in aqueous ammonia with the addition of quinoline (U.S. Pat. No. 2 072 618). A survey relating to processes for the preparation of nitrophenols will be found in Ullmanns Encyclopädie der technischen Chemie, 3rd Edition, Vol. 13, page 5 et seq. (1962).

The hydrochloric acid employed as reaction medium is normally hydrochloric acid having a concentration of 0.5 to 37 % by weight, preferably of 10 to 35 % by weight. In general, 1 part of educt is used per 2 to 15 parts of hydrochloric acid.

The preferred chlorinating agent is elemental chlorine or an alkali metal chlorate, e.g. sodium or potassium chlorate, conveniently in the form of an aqueous solution or of a solution in sulfuric acid. It is also possible to use an alkali metal hypochlorite, e.g. sodium hypochlorite, as chlorinating agent, likewise in aqueous solution. In addition, chlorination catalysts such as iodine or transition metal chlorides such as iron(III) chloride may be used.

An approximately equimolar amount of chlorinating agent is used, conveniently in an excess of 1 to 50 % by weight, per chlorine atom to be introduced. It is preferred to carry out the reaction with an excess of 10 to 20 % by weight of chlorinating agent. It is also possible to use less than an equimolar amount of chlorinating agent by adding a corresponding amount of hydrogen peroxide to the reaction mixture.

The chlorination is advantageously carried out in the temperature range from $-10°$ to $+80°$ C., preferably from 0° to 40° C. or from 5° to 40° C. Reaction temperatures above 80° C. lead to increased formation of by-products, whereas the chlorination proceeds too slowly at temperatures below $-10°$ C. When carrying out the chlorination in concentrated hydrochloric acid, a reaction temperature of 40° C. should not be exceeded, as otherwise—depending on the starting material—substantial amounts of by-products will form.

The nitroaniline or nitrophenol employed as starting material is conveniently added in the form of an aqueous suspension or of a suspension in sulfuric acid to the hydrochloric acid. Owing to the low solubility of the educts in hydrochloric acid it is advantageous to convert them into a finely dispersed form. This expedient results in a marked increase in the reaction rate and thus in the space-time yield. Conventional grinding aggregates such as stirred ball mills, sand mills or disc attrition mills are used for wet grinding the aqueous suspension. The starting material can also be comminuted by ultrasonics. Depending on the desired degree of fineness of the suspension, the grinding time is from 1 to 5 hours.

To obtain as stable a suspension as possible, the grinding may be carried out in the presence of a dispersant. Suitable dispersants are in particular anionic and nonionic surface active agents, for example adducts of ethylene oxide and fatty alcohols, alkylphenols, fatty amines or fatty acids, which are free or esterified, and also condensates of formaldehyde and aromatic sulfonic acids, lignosulfonates or oxylignosulfonates. The dispersant will normally be added to the grinding slurry in an amount of 0.1 to 5 % by weight, in particular 0.2 to 1 % by weight, based on the educt.

It often suffices if the crystalline component of the educt is ground to an average particle size of less than 100 μm.

The degree of dilution of the educt streams and the amount of hydrochloric acid charged to the reactor are calculated such that the concentration of the product in the reaction mass at the conclusion of the reaction is desirably 5 to 30 % by weight, in particular 10 to 20 % by weight. As a rule, a product concentration of more than 30 % by weight should be avoided on account of the steadily decreasing stirrability of the reaction mixture.

For working up, the reaction mixture can first be scavenged with inert gas, e.g. nitrogen, to remove excess chlorine. Final residues of chlorine, if still present, can be destroyed with bisulfite. The product, which is insoluble in the reaction mixture, can then be isolated by means of conventional separating methods, e.g. by filtration, decantation or centrifugation. The product is conveniently isolated by filtration, washed until neutral and then dried. The residual hydrochloric acid obtained as filtrate can be charged direct to the reactor for the next batch and re-used as reaction medium.

The process of this invention can be carried out batchwise as well as continuously. The known reaction vessels and apparatus are suitably employed for continuous methods, e.g. stirred flow reactors, a cascade of stirred reactors or a loop reactor. To bring the reaction to completion, if necessary, the reaction mixture is fed to another reactor, for example a tubular reactor or a cascade of stirred reactors, or simply to a second reaction vessel. The residence time of the reaction mixture in the reactor depends on the reactivity of the respective educt and on the reaction temperature.

Compared with the prior art processes, in which the educt to be chlorinated is charged to the reaction medium and then the chlorinating agent is added, the process of the present invention has the following advantages:
  almost complete conversion of the starting material;
  the product has a degree of purity higher than 98 % and can be used direct for dye synthesis;
  short reaction time and consequently a higher space-time yield
  no addition of surfactants is necessary, as foaming of the reaction mass is insignificant;
  no accumulation of chlorate and thus also no foaming of the reaction mixture caused by sudden evolution of chlorine gas;
  improved crystal form of the product, which can therefore be more readily separated, in particular filtered;
  direct re-use of the hydrochloric acid employed as reaction medium is possible;
  no rise in viscosity during the reaction, so that a uniformly good stirrability of the reaction mixture is ensured.

The chlorination process of this invention can be carried out for example as follows:

The aromatic nitro compound, e.g. 2,4-dinitroaniline, is suspended in about the same amount by weight of water and the suspension is then ground. A lignosulfonate may be added as dispersant. About 15 % by weight of hydrochloric acid is charged to the reactor (the hydrochloric acid from a previous batch may be used). 4 to 5 parts of hydrochloric acid are used per 1 part of 2,4-dinitroaniline. Then the finely ground suspension of 2,4-dinitroaniline and elemental chlorine are added simultaneously at room temperature (20°-25° C.) over 4 to 5 hours to the hydrochloric acid in the reactor. This addition may also be made at 5° C. or 40° C. instead of at room temperature.

Once the total amount of 2,4-dinitroaniline and the corresponding amount of chlorine gas—an equimolar amount and c. 10 % excess of this latter—have been added to the hydrochloric acid, the batch is allowed to react for half an hour to 1 hour and then excess chlorine is expelled with nitrogen. The product is isolated by filtration, washed until neutral and dried. The 2-chloro-4,6-dinitroaniline is obtained by this process in a yield of 95 % with a content of less than 0.5 % by weight of unreacted starting material (dinitroaniline).

The chloronitroanilines and chloronitrophenols obtained by the process of this invention are used primarily for synthesizing disperse dyes which are suitable for dyeing in particular hydrophobic fibre materials, e.g. polyester fabrics.

The invention is illustrated by the following Examples, in which parts and percentages are by weight.

EXAMPLE 1

183 parts of 2,4-dinitroaniline are suspended in 220 parts of water and the suspension is ground. 800 parts of 14.2 % hydrochloric acid are charged to a reactor. The hydrochloric acid may originate from a previous batch and, after isolation of the product, is recycled to the reactor. The aqueous suspension of dinitroaniline and a total of 78 parts of chlorine are then added simultaneously to the hydrochloric acid over 240 minutes, with the addition of dinitroaniline being made over 240 minutes, whereas the chlorine is added for a further 20 minutes, i.e. over a total time of 260 minutes. The batch is allowed to react for 30 minutes and excess chlorine is expelled over a further 30 minutes. The product is then isolated by filtration, washed until neutral and dried, affording 204 parts of 2-chloro-4,6-dinitroaniline, corresponding to a yield of 94 %. Melting point: 157.5° C. (lit. : 157°–159° C.). Analysis of gas chromatography shows that the product has the same retention time as authentic material. Comparable results are obtained by carrying out the reaction at 40° C.

EXAMPLE 2

183 parts of 2,4-dinitroaniline and 0.15 part of lignosulfonate are suspended in 220 parts of water and the suspension is ground. 800 parts of 32 % hydrochloric acid are charged to a reactor. Then 145 parts of a 33 % solution of sodium chlorate and the aqueous suspension of dinitroaniline obtained by wet grinding are added simultaneously in separate streams at 25° C. to the hydrochloric acid. The chlorate solution is added over 260 minutes and the suspension of dinitroaniline simultaneously over a somewhat shorter time of 240 minutes. The mixture is then allowed to react for 30 minutes. Excess chlorine is expelled and any chlorine residues remaining in the mixture are destroyed by adding a solution of sodium bisulfite. The product is then isolated by filtration, washed until neutral and dried, affording 204 parts of 2-chloro-4,6-dinitroaniline (yield: 94 %). Melting point: 157.5° C. (lit.: 157°–159° C.)

EXAMPLE 3

139 part of p-nitrophenol are suspended in 200 parts of water and the suspension is ground. The finely particulate suspension of p-nitrophenol so obtained is then added simultaneously with 260 parts of a 33 % solution of sodium chlorate to 1250 parts of 33 % hydrochloric acid. The simultaneous addition of educt and chlorinating agent is made at a temperature of 25° C. and such that the sodium chlorate is added over 240 minutes and the p-nitrophenol for 20 minutes longer over 260 minutes. The batch is subsequently allowed to react for 30 minutes and residual chlorine is expelled over a further 30 minutes. Any chlorine still remaining is destroyed with sodium bisulfite. The product is then isolated by filtration, washed until neutral and dried, affording 199.5 parts of 2,6-dichloro-4-nitrophenol in 99.7 % purity. The yield is 95.6 %; melting point: 119°–120° C. (lit.: 125° C.). Analysis by gas chromatography shows that the product has the same retention time as authentic material.

Comparable results are obtained by carrying out the reaction at 40° C.

EXAMPLE 4

139 parts of p-nitrophenol are suspended in 292 parts of water and the suspension is ground. A reactor is then charged with 1250 parts of 20 % hydrochloric acid which has been used as reaction medium for a previous batch and recycled to the reactor after isolation of the product. Then 156 parts of chlorine and the suspension of p-nitrophenol are added simultaneously at 25° C. to the hydrochloric acid. The suspension of nitrophenol is added over 240 minutes, whereas the simultaneous addition of chlorine is made for 20 minutes longer over 260 minutes. The batch is then allowed to react for 30 minutes and excess chlorine is expelled over a further 30 minutes. The product is isolated by filtration, washed until neutral and dried, affording 200 parts of 2,6-dichloro-4-nitrophenol (corresponding to a yield of 96 %). Melting point: 119°–120° C. (lit.: 125° C.).

EXAMPLE 5

160 parts of 2,4-dinitrophenol are suspended in 240 parts of water. Then 0.5 part of lignosulfonate (dispersant) is added to this suspension and the dinitrophenol is comminuted by ultrasonication. A reactor is charged with 210 parts of 14 % hydrochloric acid and the aqueous suspension of finely particulate 2,4-dinitrophenol and 60 parts of chlorine gas are added simultaneously at 0° C. The addition of the suspension of dinitrophenol is made over 120 minutes and the chlorine is simultaneously added over 130 minutes. When the addition of chlorine is complete, the product is isolated by filtration and washed with 250 parts of water, affording 162.4 parts of 2-chloro-4,6-dinitrophenol (corresponding to a yield of c. 83 %).

What is claimed is:

1. In a process for the preparation of a chloronitroaniline or chloronitrophenol by chlorinating a nitroaniline or nitrophenol in hydrochloric acid, wherein the improvement comprises comprises simultaneously adding to said hydrochloric acid separate streams of a nitroaniline or nitrophenol and of a chlorinating agent.

2. A process according to claim 1, which comprises chlorinating a mono- or dinitroaniline or a mono- or dinitrophenol as starting material.

3. A process according to claim 2, which comprises chlorinating 2,4-dinitroaniline or p-nitrophenol.

4. A process according to claim 1, wherein the hydrochloric acid employed as reaction medium has a concentration of 10 to 35 % by weight.

5. A process according to claim 1, wherein the chlorinating agent is elemental chlorine or an alkali metal chlorate.

6. A process according to claim 1, wherein an excess of 1 to 50 % by weight of chlorinating agent, based on the equimolar amount, is used per chlorine atom to be introduced.

7. A process according to claim 6, wherein an excess of 10 to 20 % by weight of chlorinating agent, based on the equimolar amount, is used per chlorine atom to be introduced.

8. A process according to claim 4, wherein the reaction is carried out in the temperature range from −10° to +80° C.

9. A process according to claim 8, wherein the reaction is carried out in the temperature range from 0° to 40° C.

* * * * *